United States Patent
Büscher

(10) Patent No.: US 8,377,105 B2
(45) Date of Patent: Feb. 19, 2013

(54) BONE PLATE FOR USE IN A SURGICAL PROCEDURE

(75) Inventor: Robin Büscher, Moenkeberg (DE)

(73) Assignee: Stryker Leibinger GmbH & Co., KG (DE)

( * ) Notice: Subject to any disclaimer, the term of this patent is extended or adjusted under 35 U.S.C. 154(b) by 302 days.

(21) Appl. No.: 12/603,720

(22) Filed: Oct. 22, 2009

(65) Prior Publication Data

US 2010/0106197 A1   Apr. 29, 2010

(30) Foreign Application Priority Data

Oct. 23, 2008   (EP) ..................... 08018564

(51) Int. Cl.
*A61B 17/80* (2006.01)
*A61F 5/00* (2006.01)

(52) U.S. Cl. .......................... 606/286; 606/87
(58) Field of Classification Search .............. 606/70–71, 606/280–281, 283–284, 902–906
See application file for complete search history.

(56) References Cited

U.S. PATENT DOCUMENTS

| | | | |
|---|---|---|---|
| 4,959,065 A * | 9/1990 | Arnett et al. ............... | 606/86 B |
| 5,871,548 A * | 2/1999 | Sanders et al. ............. | 623/22.36 |
| 6,978,188 B1 | 12/2005 | Christensen | |
| 2003/0055429 A1* | 3/2003 | Ip et al. ........................... | 606/69 |
| 2005/0277941 A1 | 12/2005 | Trumble et al. | |
| 2007/0118243 A1* | 5/2007 | Schroeder et al. ............ | 700/118 |
| 2007/0270850 A1 | 11/2007 | Geissler | |
| 2008/0147072 A1 | 6/2008 | Park et al. | |

FOREIGN PATENT DOCUMENTS

| | | |
|---|---|---|
| EP | 0756735 A1 | 2/1997 |
| EP | 1726265 A1 | 11/2006 |
| GB | 2334214 A | 8/1999 |
| WO | 9528688 A1 | 10/1995 |

\* cited by examiner

*Primary Examiner* — Sameh Boles
(74) *Attorney, Agent, or Firm* — Lerner, David, Littenberg, Krumholz & Mentlik, LLP

(57) ABSTRACT

A bone plate for use in a surgical procedure, in particular an osteotomy comprises a fixation portion provided with at least one opening adapted to receive a fastening device for fastening the fixation portion to a bone of a patient. A guiding portion of the bone plate having a guiding edge for guiding a bone cutting instrument during the surgical procedure, wherein the guiding portion is removably connected to the fixation portion, and wherein at least one of the fixation portion and the guiding portion has a size and shape which are customized based on anatomic data of the patient.

3 Claims, 3 Drawing Sheets

FIG 1
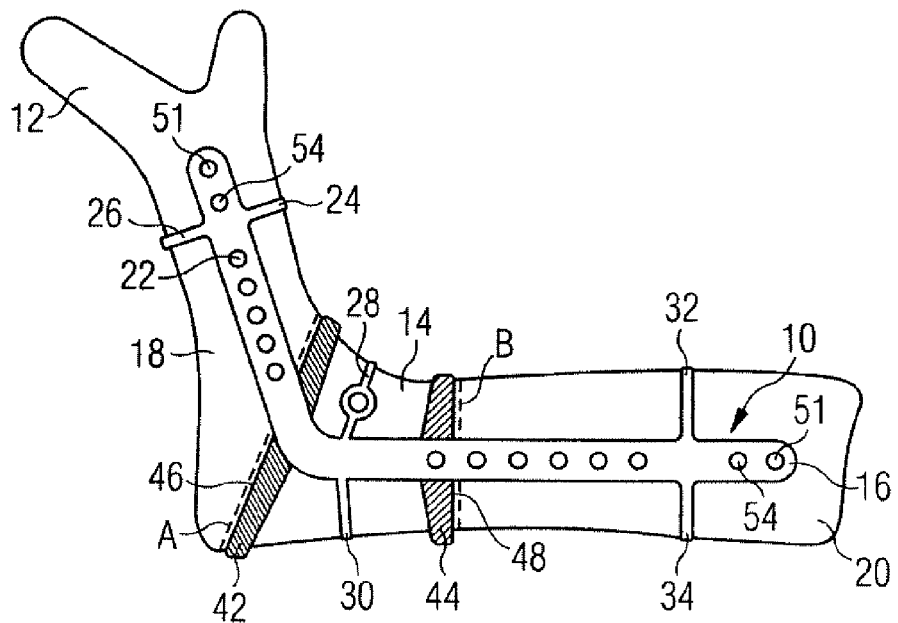
FIG 2
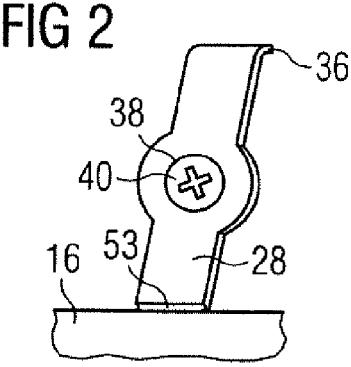
FIG 3a
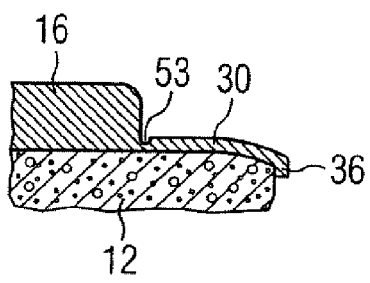
FIG 3b

BONE PLATE FOR USE IN A SURGICAL PROCEDURE

BACKGROUND OF THE INVENTION

The invention relates to a bone plate for use in a surgical procedure, in particular an osteotomy and a method of manufacturing such a bone plate.

An osteotomy is a surgical operation whereby a bone is cut to shorten or lengthen the bone, to change its alignment or to remove a diseased part of the bone. During an osteotomy surgical procedure, a guiding device having a pre-fabricated pattern is employed to guide a tool, for example a bone saw, used for cutting the bone to be treated. After temporarily fixing the guiding device to the bone, the surgeon cuts the bone along predefined cutting lines while using the guiding device for guiding the cuts. Finally, the guiding device is removed from the bone and the cut bone portions are rearranged as desired and fixed using a conventional bone plate.

BRIEF SUMMARY OF THE INVENTION

A first aspect of the present invention is a bone plate for use in an osteotomy surgical procedure which simplifies the guided cutting of the bone to be treated. In accordance with this first aspect of the present invention a method of manufacturing such a bone plate is provided.

According to one embodiment of this first aspect, the bone plate includes a fixation portion having at least one opening adapted to receive a fastening device for fastening the fixation portion to a bone of a patient. Preferably, the bone plate further includes a guiding portion provided with a guiding edge for guiding a bone cutting instrument during the surgical procedure, wherein the guiding portion is removably connected to the fixation portion, and wherein at least one of the fixation portion and the guiding portion has a size and shape which are customized based on anatomic data of the patient.

In accordance with another embodiment of this first aspect of the present invention the bone plate has a fixation portion provided with at least one opening adapted to receive a fastening device for fastening the fixation portion to a bone of a patient. Alternatively, the fixation portion may be provided with a plurality of openings. For example, the openings can be adapted to receive a bone screw and, if necessary or desired, may also be provided with an internal thread.

In accordance with yet another embodiment of this first aspect of the present invention, the bone plate further comprises a guiding portion which is provided with a guiding edge for guiding a bone cutting instrument, such as for example an oscillating bone saw or the like during the step of cutting the bone to be treated during the osteotomy. The guiding portion may for example have the form of a wing or a pair of wings extending from the fixation portion of the bone plate. The guiding edge may have a straight or curved form which may depend on the form of the cut to be excised in the bone to be treated. In case more than one cut should be carried out in the bone to be treated during the osteotomy, the guiding portion may be provided with two or more guiding edges which are suitably positioned for guiding the bone cutting instrument. Alternatively or additionally, it is possible for the bone plate to have a plurality of guiding portions. If desired, a surface of the guiding portion facing away from the bone to be treated may be sized and shaped for interaction with the bone cutting instrument. For example, the surface of the guiding portion facing away from the bone to be treated may be adapted to form a contact face against which a corresponding face of the bone cutting instrument abuts while cutting the bone being treated.

In accordance with still yet another embodiment of this first aspect of the present invention, the guiding portion is removably connected to the fixation portion. In the context of the present application the term "removably" means that the guiding portion, either manually or with the aid of a suitable instrument, such as a pincer or the like, may be removed from the fixation portion of the bone plate.

During an osteotomy, the bone plate may be temporarily fastened to the bone to be treated. The bone cutting step then can be performed, while the bone cutting instrument is guided by the guiding edge of the guiding portion provided on the bone plate. After the bone cutting step, the guiding portion is no longer necessary and can be removed from the fixation portion. After arranging the cut bone in a desired position, the cut bone portions can be fixed by fastening the fixation portion of the bone plate to the bone. The bone plate preferably fulfils the double function of guiding a bone cutting instrument during an osteotomy and fixing the bone to be treated after the osteotomy in a desired position. The use of separate devices for the bone cutting step and the fixation of the bone to be treated hence can be dispensed with.

The bone plate may be formed of any suitable bio-compatible material, for example, titanium, stainless steel or a polymeric material. If desired, the bone plate can also be formed of a bio-absorbable or bio-resorbable material.

In accordance with still yet another embodiment of this first aspect of the present invention the fixation portion and the guiding portion has a size and shape which are customized based on anatomic data of the patient. The anatomic data may be provided by the surgeon based on a preliminary examination of the patient and/or can be anatomic data obtained by computer tomography or magnetic resonance tomography procedures. In particular, the anatomic data includes the size and shape of the bone to be treated and data relating to the desired treatment of the bone, such as the course of the cut(s) to be excised in the bone during the osteotomy and the desired position of the cut bone segments after the osteotomy. The use of a customized bone plate preferably significantly simplifies the osteotomy, since adjusting steps during positioning and fastening the bone plate to the bone to be treated can be omitted or at least significantly simplified. Furthermore, the size and shape of the guiding portion is preferably adapted to the intended course of the cut to be excised in the bone during the osteotomy. The cut therefore can be excised with an enhanced precision.

In accordance with still yet another embodiment of this first aspect of the present invention the bone plate preferably further comprises a positioning portion for temporarily fastening the bone plate to the bone to be treated during the bone cutting step. Similar to the guiding portion, the positioning portion preferably also has the form of a wing extending from the fixation portion of the bone plate. The positioning portion preferably located at an end remote from the fixation portion, may be provided with a gripping portion adapted for interaction with the bone to be treated. Preferably, the gripping portion is formed by a bent end of the positioning portion and adapted to engage an edge of the bone to be treated. Preferably, the positioning portion temporarily fastens the bone plate to the bone being treated in a simple way. If necessary, the bone plate may be provided with a plurality of positioning portions, which for example, may extend from the fixation portion in various directions. Like the guiding portion, the positioning portion preferably also is removably connected to the fixation portion. For example, the positioning portion may be removed from the fixation portion either manually or with the aid of a suitable instrument.

In accordance with still yet another embodiment of this first aspect of the present invention the positioning portion of the bone plate preferably has a size and shape which are customized based on the anatomic data of the patient. The anatomic data may be provided by the surgeon based on a preliminary examination of the patient and/or may be anatomic data obtained by computer tomography or magnetic resonance tomography procedures. The use of a customized positioning portion allows to dispense with or at least to simplify adjusting steps during positioning and temporarily fastening the bone plate.

To enhance the temporary fixation of the bone plate to the bone to be treated the positioning portion may be provided with an opening adapted to receive a fastening device. For example, the opening provided in the positioning portion may be adapted to receive a bone screw. If desired, an internal thread may be provided in the opening. In case the bone plate comprises more than one positioning portions, either a selected number of positioning portions or all positioning portions may be provided with respective openings for receiving corresponding fastening devices.

In accordance with still yet another embodiment of this first aspect of the present invention to facilitate removal of the guiding portion from the fixation portion of the bone plate, a notch may be provided in a transition region between the fixation portion and the guiding portion. Similarly, to facilitate removal of the position portion from the fixation portion a notch may be provided in a transition region between the fixation portion and the positioning portion. The notch(es) define(s) a predetermined breaking point such that the force which is necessary to separate the guiding portion and/or the positioning portion from the fixation portion is significantly reduced.

In accordance with still yet another embodiment of this first aspect of the present invention the bone plate preferably includes a distance opening. The distance opening may be disposed at a location on the fixation portion which coincides with a location on the bone to be treated prior to arranging the bone in a desired new position during the osteotomy at which the fixation portion should be fastened to the bone to be treated after the bone is arranged in the desired new position. In other words, the distance opening is disposed at a location on the fixation portion which coincides with a location on the bone to be treated prior to rearranging the bone, which after rearranging the bone should serve as a fixation position of the bone to the fixation portion of the bone plate.

During an osteotomy surgical procedure the distance opening thus can be used as a pattern for drilling a respective hole into the bone prior to rearranging the bone at a location at which the bone should be fastened to the fixation portion of the bone plate after rearranging the bone. The hole drilled into the bone defines the desired fastening position of the fixation portion of the bone plate to the bone. In case the bone plate during the osteotomy is temporarily released from the bone to be treated, so as to rearrange the bone and/or to remove the guiding portion and/or the positioning portion from the fixation portion of the bone plate, the fixation of the fixation portion of the bone plate to the bone at a desired location is significantly simplified.

A second aspect of the present invention is an inventive method of manufacturing a bone plate for use in a surgical procedure, in particular an osteotomy. Preferably, the bone plate includes a fixation portion having at least one opening adapted to receive a fastening device for fastening the fixation portion to a bone. Preferably, the bone plate further includes a guiding portion having a guiding edge for guiding a bone cutting instrument during the osteotomy, wherein the guiding portion is removably connected to the fixation portion. Preferably, the fixation portion and the guiding portion are fabricated with a customized size and shape based on anatomic data of a patient. Preferably, the anatomic data can be anatomic data provided by the surgeon or anatomic data obtained by computer tomography and/or magnetic resonance tomography procedures. Preferably, the anatomic data includes the size and shape of the bone to be treated and may also include data relating to the desired treatment of the bone, such as the course of the cut(s) to be excised in the bone during the osteotomy and the desired position of the cut bone segments after the osteotomy surgical procedure.

Preferably, the fixation portion and the guiding portion of the bone plate are formed integrally in only one manufacturing step.

In accordance with one embodiment of this second aspect of the present invention the positioning portion of the bone plate has a gripping portion, the gripping portion being adapted for interacting with the bone so as to temporarily fasten the bone plate to the bone, wherein the positioning portion is removably connected to the fixation portion. Preferably, the fixation portion is fabricated with a customized size and shape based on the anatomic data of the patient.

Preferably, the positioning portion is formed integrally with the fixation portion and the guiding portion in only one manufacturing step. In case more than one guiding portion and/or more than one positioning portion should be formed on the bone plate, preferably all guiding portions and/or all positioning portions are formed integrally with the fixation portion of the bone plate in only one manufacturing step.

For example, the bone plate may be formed by cutting or milling a solid material or by sintering.

A third aspect of the present invention is a surgical procedure including obtaining anatomic data of a patient. The anatomic data might be obtained by the surgeon based on a preliminary examination of the patient and/or can be anatomic data obtained by computer tomography or magnetic resonance tomography procedures. Preferably, the anatomic data includes the size and shape of the bone to be treated and data relating to the desired treatment of the bone, such as the course of the cut(s) to be excised in the bone during the surgical procedure and the desired position of the cut bone segments after the surgical procedure. The surgical procedure preferably further includes manufacturing the bone plate, wherein a fixation portion of the bone plate has at least one opening adapted to receive a fastening device for fastening the fixation portion to a bone of the patient. Preferably, the bone plate has a guiding portion having a guiding edge for guiding a bone cutting instrument during the surgical procedure, wherein the guiding portion is removably connected to the fixation portion. Preferably, the guiding portion and the fixation portion are fabricated having a customized size and shape based on the anatomic data of the patient. Preferably, the bone plate is temporarily fastened to the bone of the patient. Thereafter, the bone to be treated is cut along a desired cutting line by means of a bone cutting instrument, such as for example a bone saw, wherein the bone cutting instrument is guided by the guiding edge of the guiding portion of the bone plate. The guiding portion may then be removed from the fixation portion of the bone plate and the bone to be treated is preferably arranged in a desired position. The fixation portion of the bone plate may then be fastened to the bone to be treated. Preferably, the surgical procedure is an osteotomy.

In accordance with one embodiment of this third aspect of the present invention, a positioning portion of the bone plate has a gripping portion, the gripping portion being adapted for interacting with the bone so as to temporarily fasten the bone plate to the bone, wherein the positioning portion is removably connected to the fixation portion. The positioning portion and the fixation portion may be fabricated having a customized size and shape based on the anatomic data of the patient.

Preferably, the bone plate is temporarily fastened to the bone to be treated by means of the positioning portion. Similar to the guiding portion, the positioning portion may be removed from the fixation portion of the bone plate prior to fastening the fixation portion of the bone plate to the bone to be treated.

If desired or necessary, the bone plate may be temporarily fastened to the bone to be treated by inserting a fastening device, such as a bone screw, into an opening provided in the positioning portion of the bone plate.

After the bone to be treated is cut, the bone plate may be released from the bone to be treated for removing the guiding portion and/or the positioning portion from the fixation portion of the bone plate and/or to arrange the bone to be treated in a desired position. The guiding portion and/or the positioning portion may be removed from the fixation portion of the bone plate either manually or with the aid of a suitable instrument, such as a pincer.

To simplify the fixation of the bone plate to the bone to be treated after temporarily releasing the bone plate from the bone and/or after rearranging the bone, prior to arranging the bone to be treated in a desired new position, a hole may be drilled into the bone at a position defined by the distance opening provided in the fixation portion of the bone plate.

BRIEF DESCRIPTION OF THE DRAWINGS

A preferred embodiment of the present invention now will be described in greater detail based on the accompanying schematic drawings, wherein:

FIG. 1 shows a bone plate temporarily fastened to the mandible of a patient during an osteotomy.

FIG. 2 shows a detailed view of a first positioning portion of the bone plate shown in FIG. 1.

FIGS. 3a and 3b show detailed views of a second positioning portion of the bone plate shown in FIG. 1.

DETAILED DESCRIPTION

Figure 4:
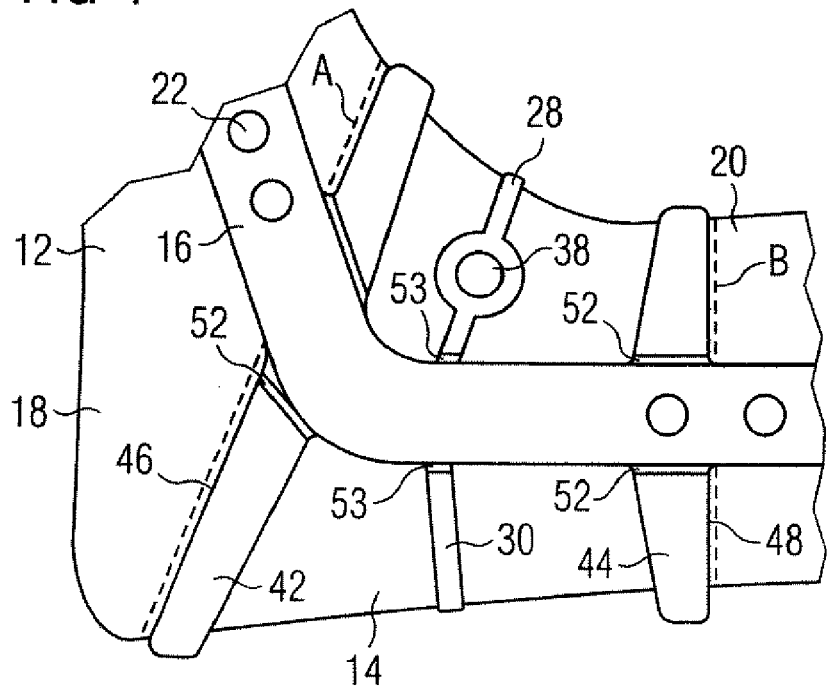
FIG. 4 shows a detailed view of a central portion of the bone plate shown in FIG. 1.

FIG. 1 shows a bone plate 10 which is temporarily fixed to a mandible 12 of a patient, wherein the mandible 12 is intended to be treated by a surgical procedure, such as an osteotomy so as to remove a diseased bone portion 14. The bone plate 10 comprises a plate-shaped fixation portion 16, which is adapted to be fastened to the mandible 12 after the osteotomy so as to fix cut bone portions 18, 20 in a desired position. The fixation portion 16 is provided with a plurality of openings 22 for receiving suitable fastening devices, such as bone screws.

For temporarily fastening the bone plate 10 to the mandible 12, bone plate 10 is provided with positioning portions 24, 26, 28, 30, 32, 34. The positioning portions 24, 26, 28, 30, 32, 34 are substantially wing-shaped and extend in pairs in substantially opposite directions from the fixation portion 16 of the bone plate 10. As becomes apparent from FIGS. 3a and 3b, an end of the positioning portions 24, 26, 28, 30, 32, 34 remote from the fixation portion 16 of the bone plate 10 is bent so as to form a gripping portion 36 adapted for interacting with the bone 12 to be treated. In particular, the gripping portion 36 is adapted to engage an edge of the mandible 12 so as to temporarily fasten the bone plate 10 to the mandible 12.

To enhance fixation of the bone plate 12 to the mandible 12 during the osteotomy, a positioning portion 28 in addition to a gripping portion 36 is provided with an opening 38. As shown in FIG. 2, opening 38 is adapted to receive a fastening device 40, such as a bone screw. Bone plate 10, as shown in FIG. 1, includes a positioning portion 28 having a fastening device receiving opening 38. A plurality of positioning portions 24, 26, 28, 30, 32, 34 may include fastening device receiving openings 38.

The bone plate 10 preferably further comprises two guiding portions 42, 44, each of which are shaped as a pair of wings extending from the fixation portion 16 of the bone plate 10. Each guiding portion 42, 44 is provided with a guiding edge 46, 48. The guiding edges 46, 48 of the guiding portions 42, 44 each define a cutting line A, B respectively along which the mandible 12 is intended to be cut during the osteotomy.

The entire bone plate 10, including the fixation portion 16, the guiding portions 42, 44 and the positioning portions 24, 26, 28, 30, 32, 34 have a customized size and shape based on anatomic data of the patient. The anatomic data is preferably obtained by computer tomography or magnetic resonance tomography procedures and processed by means of suitable software applications. The anatomic data preferably includes the size and shape of the mandible 12 to be treated and data relating to the desired treatment of the mandible 12, such as the course of the cut to be excised in the mandible 12 during the osteotomy and the desired position of the cut bone portions 18, 20 after the osteotomy.

Figure 5:
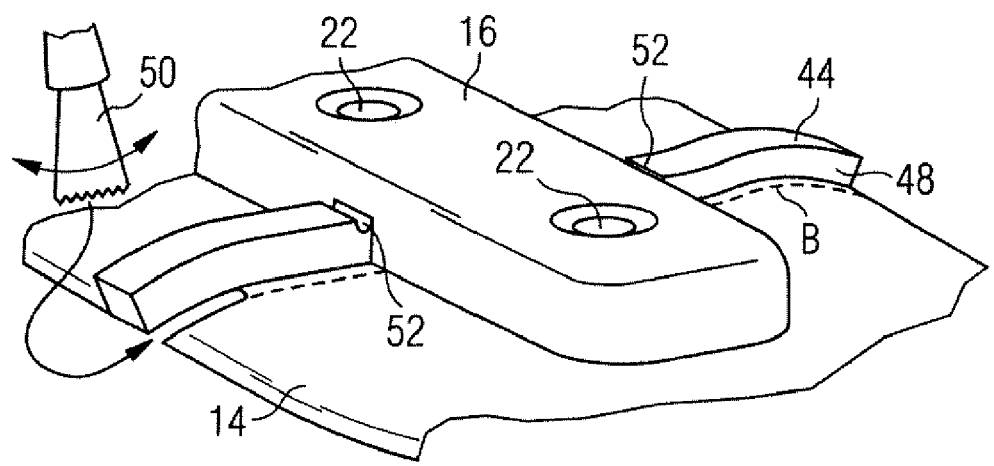
FIG. 5 shows a detailed view of a guiding portion of the bone plate shown in FIG. 1.
Figure 6:
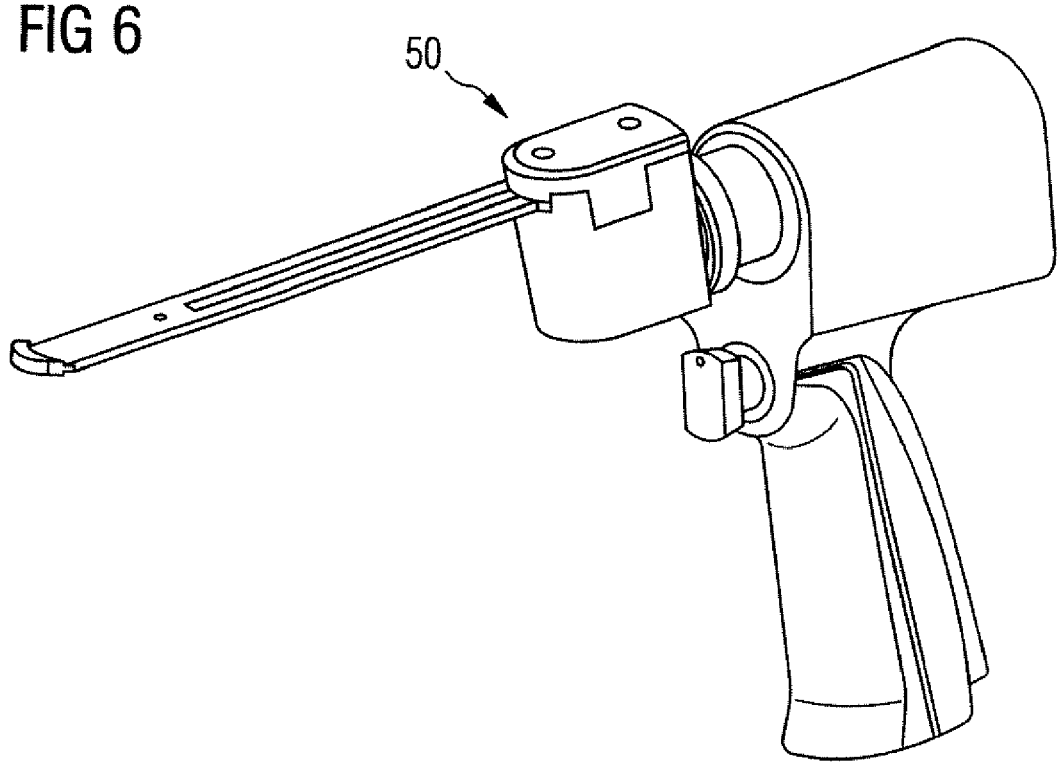
FIG. 6 shows an oscillating bone saw which may be used in an osteotomy carried out with the aid of a bone plate shown in FIG. 1.

As shown in FIG. 5, during the osteotomy, a bone cutting instrument 50, such as a bone saw shown in FIG. 6, is guided by the guiding edge 46, 48 of the guiding portions 43, 44. Hence, the mandible 12 can easily and reliably be cut along a length of the desired cutting line A, B extending from the edges of the mandible 12 to the fixation portion 16 of the bone plate 10.

Thereafter, holes are drilled into the cut bone portions 18, 20, wherein distance openings 51 in the fixation portion 16 of the bone plate 10 serve as a pattern so as to define the location of the holes drilled into the bone portions 18, 20.

After the guided cutting step and the drilling step, the fastening device 40 is released and the bone plate 10 is detached from the mandible 12. The cuts along the cutting lines A, B then can be finalized and the bone portions 18, 20 are arranged in a new desired position. For example, the cut bone portions 18, 20 are disposed adjacent to each other. It is, however, also possible to position a suitable implant between the cut bone portions 18, 20.

After the bone plate 10 is detached from the mandible 12, the positioning portions 24, 26, 28, 30, 32, 34 and the guiding portions 42, 44 are removed from the fixation portion 16. The removing step can be performed either manually or by the aid of a suitable instrument, such as a pincer. To facilitate the removal of the guiding portions 42, 44 from the fixation portion 16 of the bone plate 10, notches 52 are provided in transition regions between the fixation portion 16 and the guiding portions 42, 44. Similarly, to facilitate the removal of the positioning portions 24, 26, 28, 30, 32, 34 from the fixation portion 16 of the bone plate 10, notches 53 are provided in transition regions between the fixation portion 16 and the positioning portions 24, 26, 28, 30, 32, 34. Each of the notches 52, 53 defines a predetermined breaking point such that the force which is necessary to separate the guiding portions 42, 44 and the positioning portions 24 to 34 from the fixation portion 16 is significantly reduced.

After arranging the bone portions 18, 20 in the desired position and after removing the positioning portions 24, 26, 28, 30, 32, 34 and the guiding portions 42, 44 from the fixation portion 16 the bone plate 10, the fixation portion 16 of the bone plate 10 is preferably refastened to the mandible 12 so as to fix the cut bone portions 18, 20 in place. The positioning of the bone plate 10 on the bone portions 18, 20 is facilitated by the holes drilled into the bone portions 18, 20 by the aid of the distance openings 51, since these holes, after arranging the bone portions 18, 20 in the desired position, coincide with respective positioning openings 54 provided in the fixation portion 16 of the bone plates 10.

Upon refastening the bone plate 10 to the mandible 12, fastening devices, such as bone screws are inserted into the positioning openings 54 coinciding with the holes drilled into the bone portions 18, 20 prior to rearranging the bone portions 18, 20. Thereafter, final fixation of the bone plate 10 to the bone portions 18, 20 is accomplished by inserting a sufficient number of fastening devices, such as bone screws, into the openings 22 of the fixation portion 16.

The invention claimed is:

1. An elongated bone plate having opposing first and second side surfaces, the elongated bone plate for use in a surgical procedure comprising: a fixation portion having at least one opening adapted to receive a fastening device for fastening the fixation portion to a bone of a patient; a guiding portion projecting outwardly from the opposing first and second side surfaces of the elongated bone plate, the guiding portion provided with a flat guiding edge for guiding a bone cutting instrument during the surgical procedure; and positioning portions projecting outwardly from the opposing first and second side surfaces of the elongated bone plate, wherein one of the positioning portions having at least one hole for receiving a fastening device for temporarily fastening the bone plate to the bone, each of the positioning portions being provided with a bent gripping portion at an end thereof, wherein the guiding portion and the positioning portions are removably connected to the fixation portion, the guiding portion and positioning portions including a notch provided in a transition region with the fixation portion so as to facilitate removal of the guiding portion and positioning portions from the fixation portion, and wherein at least one of the fixation portion and the guiding portion has a size and shape which are customized based on anatomic data of the patient.

2. The bone plate of claim 1, wherein the gripping portion is adapted for interacting with the bone so as to temporarily fasten the bone plate to the bone, and wherein the positioning portions have a size and shape which are customized based on the anatomic data of the patient.

3. The bone plate of claim 1, wherein a distance opening is provided in the fixation portion, the distance opening being disposed at a location on the fixation portion which coincides with a location on the bone prior to arranging the bone in a desired new position during the surgical procedure at which the fixation portion should be fastened to the bone after the bone is arranged in the desired new position.

* * * * *